United States Patent
Rogozinski

Patent Number: 5,370,875
Date of Patent: Dec. 6, 1994

[54] TOPICAL, ANTIMICOBIAL POWDERS OF CHLOROXYLENOL AND CHLORHEXIDINE DIACETATE

[75] Inventor: Wallace J. Rogozinski, Azusa, Calif.

[73] Assignee: C. R. Bard, Inc., Murray Hill, N.J.

[21] Appl. No.: 822,113

[22] Filed: Jan. 17, 1992

[51] Int. Cl.$^5$ .............................................. A01N 25/12
[52] U.S. Cl. .................................... 424/405; 424/408; 424/409; 424/401; 424/65; 424/489; 424/724
[58] Field of Search ............... 424/405, 618, 406, 493, 424/498

[56] References Cited

U.S. PATENT DOCUMENTS 4,321,257 3/1982 Sipos ..................................... 424/80

OTHER PUBLICATIONS

Goodman & Gillman; Pharmacological Basis of Therapeutic, 4th edition, p. 989, 1970.
Physicians Desk Reference—39th edition, 1985, p. 1581, 829.

*Primary Examiner*—Thurman K. Page
*Assistant Examiner*—Neil Levy
*Attorney, Agent, or Firm*—G. Donald Weber, Jr.

[57] ABSTRACT

A highly absorptive, topical, dusting powder which contains two safe and effective antimicrobial agents such as chlorhexidine diacetate and chloroxylenol, sodium and potassium alumino silicate, a unique, odor-eliminating molecular sieve. The natural cornstarch base of the powder has been supplemented with Magnesium-L-Lactate for its anti-pruritic properties.

10 Claims, No Drawings

TOPICAL, ANTIMICOBIAL POWDERS OF CHLOROXYLENOL AND CHLORHEXIDINE DIACETATE

BACKGROUND

1. Field of the Invention

This invention is directed to a topical, antimicrobial powder in general, and to such a powder which includes a molecular sieve, in particular.

2. Prior Art

Superficial topical infections are commonly a consequence of a primary disease process such as chronic urinary incontinence or directly related to a contagious nosocomial or endemic source. Prolonged moist or wet skin conditions often lead to maceration and other changes in skin integrity which provide the opportunity for normally saprophytic bacteria and fungi to invade the site and establish an infection. The micro-organism most prevalent in "moist environment" infections is *Candida albicans*, a yeast-like fungus. This type of infection is usually characterized by erythema, edema and intense pruritus.

Other localized, topical infections may be bacterial in origin and the direct result of skin-to-skin contact with a contaminated vector. One of the most serious nosocomially acquired contagious bacterial infections is Methicillin Resistant *Staphylococcus aureus* which is often implicated in skin cellulitis, impetigo, boils and wound infections.

On occasion, the etiological agent of the infection is a combination of bacteria and fungi. This is referred to as a mixed infection, wherein dissimilar micro-organisms co-exist to the benefit of both and to the detriment of the host.

Standard therapy for topical infections consists of applications of antimicrobial creams, ointments or powders to the site and/or the administration of parenteral or oral antibiotics.

Most topically applied antimicrobial agents have a very limited range of effectiveness and are, in some instances, specific for one species of micro-organism. For example, nystatin, in all forms, e.g. powder, ointment and cream, is considered useful in treating only those infections caused by Candida sp., and is, therefore, inappropriate for bacterial infections. Moreover, micro-organism specific antimicrobial agents are not only ineffective in the treatment of mixed infections, even when one of the micro-organisms has a proven sensitivity to the antimicrobial agent used, but can increase the risk of a superinfection by altering the natural controls of the symbiotic relationship which exists.

Principally through the combined action of chlorhexidine diacetate and chloroxylenol, the present invention provides complete and rapid, broad-spectrum antisepsis. The effective microbicidal range that it encompasses includes both saprophytic and pathogenic bacteria and fungi or a mixture thereof. As a consequence, it provides a useful treatment of pure and mixed infections.

Foul odors usually accompany topical infections, especially those infections secondary to chronic urinary incontinence where the urea component of urine is decomposed by urea-splitting skin bacteria into ammonia. Ammonia is the chemical basis of most objectional odors associated with urinary incontinence. The current invention has been enriched with a molecular sieve which is an aluminosilicate compound that has the unique ability to absorb and trap odor molecules within its porous crystalline internal structure. The molecular sieve enhancement in the present invention provides the means to control disagreeable odors related to localized infection and incontinence.

Inflammation and pruritus represent diagnostic clues of the presence of a topical infection. Infection is often confirmed by the identification of the etiological agent through the use of microscopic and microbiological culture techniques. Magnesium-L-Lactate has been added to the invention to impart an antipruritic action to the infection site.

SUMMARY OF THE INSTANT INVENTION

The useful purpose of the present invention is to effectively treat topical infections of a bacterial or fungal nature through the combined action of two safe and effective antimicrobial agents, typically, chlorhexidine diacetate and chloroxylenol. Symptoms associated with infection, such as pruritus, are relieved by the use of the topical antipruritic, Magnesium-L-Lactate, and foul odors produced at the infection site as the result of microbial action are controlled by the unique odor-absorbing agent, sodium potassium alumino silicate, a molecular sieve of which a suitable one is commercially distributed as ABSCENTS ® powder, a UOP trademark.

Cornstarch represents a large constituent of the powder and operates as a base thereto. In addition, the cornstarch absorbs moisture on the skin surface which can otherwise lead to skin maceration and thereby increase the risk of localized infection. Anti-caking components can be added to the powder to effectively prevent caking of the powder.

DESCRIPTION OF A PREFERRED EMBODIMENT

This invention is directed to a topical, antimicrobial powder formed of a number of constituents.

In a preferred embodiment, a pair of antimicrobial agents are utilized. The preferred antimicrobial agents used in the compound and compositions of this invention are chloroxylenol and chlorhexidine diacetate, although agents of similar configuration can be utilized. In the preferred embodiment, chloroxylenol is the substituted phenol that conforms to the empirical chemical formula $C_8H_9C_{10}$ as shown structurally below:

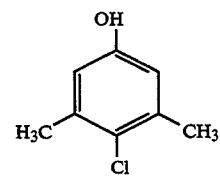

Similarly, chlorhexidine diacetate is a salt of chlorhexidine and acetic acid which conforms generally to the formula $C_{22}H_{30}Cl_2N_{10}\,2C_2H_4O_2$ as shown structurally below:

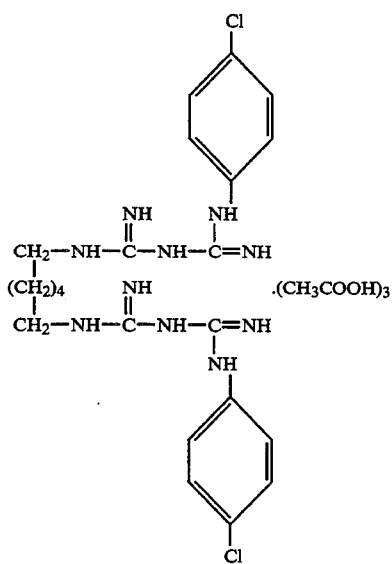

Chloroxylenol and chlorhexidine diacetate are antimicrobial components, each of which comprises about 1% of the powder described herein. The preparation of these antimicrobial compounds is well known and clearly delineated in chemical literature. The essential characteristics of these compounds are antimicrobial activity in that they tend to destroy microbial bacteria.

For example, chlorhexidine diacetate has an affinity for bacteria due to the interaction of the positively charged molecules of the compound with negatively charged groups of molecules on the bacterial cell wall. The interaction of the molecules tends to increase the permeability of the cell wall. Chlorhexidine diacetate can then penetrate the cytoplasm, whereupon important organic and inorganic constitutents seep out of the cell causing death of the organism. Chloroxylenol is believed to act primarily by denaturing cell proteins and damaging cell membranes with the net effect of destroying the cell.

While two preferred agents are recited, other such agents are known in the art and at least some of these agents may be substituted. It is noted that chloroxylenol belongs to the family of halogenated phenols which includes, inter alia, hexachlorophene, hexylresorcinal and the like. Likewise, chlorhexidine belongs to the family of bisdiguanidines having antimicrobial activity which includes, inter alia, alexidine, ambazone, picloxydine and the like.

A chemically modified molecular sieve comprises about 5% w/w of the current invention. Several suitable sieves are available on the market. One such sieve is a powder distributed commercially as ABSCENTS, a registered trademark of UOP, and covered by U.S. Pat. No. 4,795,482. A preferred embodiment of such sieve is described as potassium sodium alumino silicate which conforms generally to the composition of zeolites such as $N_2O:Al_2O_3:xSiO_2:xHO_4$. Potassium sodium alumino silicate has the ability to adsorb noxious odors associated with localized infection, as well as the gaseous by-products of microbial decomposition. The molecular sieve constituent of the current invention thereby demonstrates exceptional deodorizing properties. Of course, similar molecular sieves can be utilized and can comprise a range of 3% to 10% of the overall combination.

In a preferred embodiment, a topical anti-pruritic is utilized. One preferred example of the anti-pruritic is Magnesium-L-Lactate, which conforms, generally, to the chemical formula $C_6H_{10}M_9O_6$. In the preferred embodiment, the Magnesium-L-Lactate comprises about 3% w/w of the formula and functions as a topical anti-pruritic. Of course, other similar anti-pruritic agents can be utilized and can comprise 1% to 10% of the overall combination.

Allantoin, which conforms to the empirical formula $C_4H_{10}N_4O_3$, comprises about 1% w/w of the current invention and functions as a skin protectant. Of course, other protectants can be used within a typical range of 0.5% to 5% of the combination.

Cornstarch, a carbohydrate polymer derived from corn of various types, composed of 25% amylose and 75% amylopectin, comprises about 73% w/w of the formulation and functions as a moisture absorbing agent. Of course, other similar moisture absorbing agents can be used with a range of 40% to 90% of the overall combination.

In the preferred embodiment, zinc stearate, $Z(C_{18}H_{35}O_2)_2$, and Dry Flo, a starch ester derivative containing hydrophobic groups, comprise about 2% and 15% w/w, respectively, of the invention. These components are incorporated into the formulation for their anti-caking properties. Other suitable anti-caking materials can be used with ranges of 1% to 20% in the overall combination.

TEST PREPARATION

The antimicrobial effectiveness of the present invention was evaluated against a wide range of bacterial and fungal organisms, especially those commonly found on human skin. Representative demonstrated test results are presented herewith. The tests were performed under the guidelines of the United States Pharmacopeia XXII 1990, <51>, <61> and <71>.

Freeze dried cultures of all organisms (except lab isolate) were obtained from American type culture collection and revived following their instructions. The stock cultures of bacteria were maintained on tryptic soy agar slants and the stock cultures of Candida albicans and Aspergillus niger were maintained on Sabouraud dextrose agar slants.

Stock cultures of bacteria were transferred onto tryptic soy agar medium and incubated at 35° C. for eighteen to twenty-four hours prior to use. Stock cultures of Candida albicans and Aspergillus niger were transferred on Sabouraud dextrose agar and incubated at room temperature for twenty-four to forty-eight hours and seventy-two hours, respectively. Cultures were harvested by washing the surface of the growth medium with sterile buffered saline solution and sterile dacron swabs. All suspensions of cultures were centrifuged and the cells then harvested. Required inoculum levels of organisms were obtained by adding sterile buffered saline solution and adjusting it to a predetermined concentration using a Spectronic 20 spectrophotometer.

TEST PROCEDURE

1. An aerobic sterility test was performed on the antimicrobial powder prior to the test.

2. Three batches of powder were produced; one for direct test, one for accelerated aging test, and one for control purposes without the antimicrobial agents.

3. 20 gms of each batch of antimicrobial powder was weighed in sterile jars and wetted with 10 ml sterile buffered saline solution.

4. Inoculum was prepared as above and each pre-weighed sample of antimicrobial powder was inoculated with approximately $1 \times 10^6$ organisms/gm of test product.

5. 1 gm of inoculated product was transferred to 9 ml of sterile buffered saline solution at intervals of 0, 5, 10, 15, 20, 25, 30 and 60 minutes.

6. Each antimicrobial powder/saline mixture was thoroughly mixed and 1 ml of each diluted mixture was transferred onto tryptic soy agar for exposure to bacteria and Sabouraud dextrose agar for exposure to Candida albicans and Aspergillus niger.

7. All bacterial plates were incubated at 35° C. for forty-eight hours; all Candida albicans and Aspergillus niger plates were incubated at room temperature for forty-eight and seventy-two hours, respectively.

8. Plate counts were performed and percent reduction of the inoculum was determined.

TABLE I

TEST ORGANISMS

| | |
|---|---|
| 1. *Candida albicans* | ATCC #1-231 |
| 2. *Aspergillus niger* | ATCC #16404 |
| 3. *Pseudomonas aeruginosa* | ATCC #9027 |
| 4. *Pseudomonas species* | Lab. Isolate |
| 5. *Staphylococcus aureus* | ATCC #6538 |
| 6. Methicillin Resistant *Staphylococcus aureus* | ATCC #33591 |
| 7. *Escherichia coli* | ATCC #8739 |

TABLE II

Effectiveness of the antimicrobial powder on test organisms shown as percent reduction of organism after contact time up to 60 minutes.
PERCENT REDUCTION OF TEST ORGANISMS

| Test Organisms | Minutes | | | | | | | |
|---|---|---|---|---|---|---|---|---|
| | 0 | 5 | 10 | 15 | 20 | 25 | 30 | 60 |
| 1. See | 0 | 99.81 | 99.98 | 99.99 | 100 | 100 | 100 | 100 |
| 2. TABLE | 0 | 99.95 | 99.96 | 100 | 100 | 100 | 100 | 100 |
| 3. I | 0 | 99.99 | 99.99 | 99.99 | 100 | 100 | 100 | 100 |
| 4. | 0 | 99.98 | 99.99 | 100 | 100 | 100 | 100 | 100 |
| 5. | 0 | 99.99 | 99.99 | 100 | 100 | 100 | 100 | 100 |
| 6. | 0 | 99.99 | 99.99 | 99.99 | 99.99 | 100 | 100 | 100 |
| 7. | 0 | 99.98 | 99.99 | 100 | 100 | 100 | 100 | 100 |

TABLE III

Effectiveness of the antimicrobial powder following accelerated aging process.
PERCENT REDUCTION OF TEST ORGANISMS

| Test Organisms | Minutes | | | | | | | |
|---|---|---|---|---|---|---|---|---|
| | 0 | 5 | 10 | 15 | 20 | 25 | 30 | 60 |
| 1. See | 0 | 99.97 | 99.98 | 99.99 | 100 | 100 | 100 | 100 |
| 2. TA- | 0 | 99.88 | 99.97 | 99.99 | 100 | 100 | 100 | 100 |
| 3. BLE | 0 | 99.99 | 99.99 | 99.99 | 100 | 100 | 100 | 100 |
| 4. I | 0 | 99.99 | 99.99 | 100 | 100 | 100 | 100 | 100 |
| 5. | 0 | 99.98 | 99.99 | 99.99 | 100 | 100 | 100 | 100 |
| 6. | 0 | 99.97 | 99.99 | 99.99 | 99.99 | 99.99 | 100 | 100 |
| 7. | 0 | 99.99 | 99.99 | 100 | 100 | 100 | 100 | 100 |

TABLE IV

Effectiveness of the antimicrobial powder without the active ingredients chloroxylenol and chlorhexidine diacetate.
PERCENT REDUCTION OF TEST ORGANISMS

| Test Organisms | Minutes | | | | | | | |
|---|---|---|---|---|---|---|---|---|
| | 0 | 5 | 10 | 15 | 20 | 25 | 30 | 60 |
| 1. See | 0 | 0 | 0 | 0 | 0 | 0 | 0 | 0 |
| 2. TABLE I | 0 | 0 | 0 | 0 | 0 | 0 | 0 | 0 |
| 3. | 0 | 0 | 0 | 0 | 0 | 0 | 0 | 0 |
| 4. | 0 | 0 | 0 | 0 | 0 | 0 | 0 | 0 |
| 5. | 0 | 0 | 0 | 0 | 0 | 0 | 0 | 0 |
| 6. | 0 | 0 | 0 | 0 | 0 | 0 | 0 | 0 |
| 7. | 0 | 0 | 0 | 0 | 0 | 0 | 0 | 0 |

CONCLUSION

The antimicrobial powder proved to be extremely effective against the test organisms. All test organisms were reduced by at least 99.81% within the first five minutes of contact time in-vitro, as shown in Table II. Moreover, 100% reduction of all test organisms was observed within 25 minutes of contact time. Similarly, the antimicrobial powder which was subjected to accelerated aging conditions (45° C. for three months=one year at room temperature) did not show any detectable loss in antimicrobial activity as shown in Table III. On the other hand, as shown in Table IV, there was 100% recovery of the test organisms from the control test (the antimicrobial powder without active ingredients chlorhexidine diacetate and chloroxylenol).

Thus, there is shown and described a unique topical antimicrobial powder. While this description is directed to a particular embodiment, it is understood that those skilled in the art may conceive modifications and/or variations to the specific embodiments shown and described herein. Any such modifications or variations would fall within the purview of this description are intended to be included therein as well. It is understood that the description herein is intended to be illustrative only and is not intended to be limitative. Rather, the scope of the invention described herein is limited only by the claims appended hereto.

I claim:

1. A topical antimicrobial powder comprising the combination of,
   a pair of antimicrobial agents,
   said microbial agents belong to the halogenated phenols and bisdiguanidines, respectively,
   a molecular sieve,
   an anti-pruritic agent,
   a skin protectant, and
   a moisture absorbing agent.

2. The powder recited in claim 1 wherein, said pair of antimicrobial agents comprise chloroxylenol and chlorhexidine diacetate, respectively.

3. The powder recited in claim 1 wherein, said molecular sieve comprises a composition of zeolites.

4. The powder recited in claim 1 wherein, said skin protectant comprises allantoin.

5. The powder recited in claim 1 wherein, said moisture absorbing agent comprises a carbohydrate polymer.

6. The powder recited in claim 5 wherein, said polymer comprises cornstarch.

7. The powder recited in claim 1 including, an anti-caking agent.

8. The powder recited in claim 1 wherein, said anti-caking agent comprises a zinc stearate.

9. A topical antimicrobial powder comprising the combination of the following weight percentages of consituents,
- a pair of antimicrobial agents,
- said pair of antimicrobial agents comprise chloroxylenol and chlorhexidine diacetate, each of which comprises about 1% of the powder, respectively,
- a molecular sieve comprising a composition of zeolites which comprises about 3–10% of the powder,
- an anti-pruritic agent which comprises about 1–10% of the powder,
- a skin protectant comprising allantoin which comprises about 0.5% to 5% of the powder,
- a moisture absorbing agent comprising a carbohydrate polymer which comprises about 40–90% of the powder, and
- an anti-caking agent comprising a zinc stearate which comprises about 2–15% of the powder.

10. A topical antimicrobial powder comprising the combination of the following weight percentages of constituents,
- a pair of antimicrobial agents, each of which comprises about 1% of the powder,
- a molecular sieve which comprises about 3–10% of the powder,
- an anti-pruritic agent which comprises about 1–10% of the powder,
- a skin protectant which comprises about 0.5% to 5% of the powder,
- a moisture absorbing agent which comprises about 40–50% of the powder, and
- an anti-caking agent which comprises about 2–15% of the powder.

* * * * *